(12) United States Patent
Hazin et al.

(10) Patent No.: US 7,229,946 B2
(45) Date of Patent: Jun. 12, 2007

(54) CATALYST COMPOSITION FOR THE SELECTIVE CONVERSION OF ALKANES TO UNSATURATED CARBOXYLIC ACIDS, METHOD OF MAKING AND METHOD OF USING THEREOF

(75) Inventors: Paulette N. Hazin, Houston, TX (US); Paul E. Ellis, Jr., Sugar Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 336 days.

(21) Appl. No.: 10/806,862

(22) Filed: Mar. 23, 2004

(65) Prior Publication Data

US 2004/0192966 A1    Sep. 30, 2004

(51) Int. Cl.
    B01J 23/00    (2006.01)
    B01J 21/00    (2006.01)
    B01J 20/00    (2006.01)

(52) U.S. Cl. .................. 502/311; 502/248; 502/255; 502/263; 502/312; 502/313; 502/314; 502/315; 502/316; 502/317; 502/322; 502/344; 502/353; 502/354; 502/349; 502/350; 502/355; 502/407; 502/415; 502/439

(58) Field of Classification Search .......... 502/248, 502/255, 263, 311, 312, 313, 314, 315–317, 502/322, 344, 353, 354, 349, 350, 355, 407, 502/415, 439
See application file for complete search history.

(56) References Cited

U.S. PATENT DOCUMENTS

| | | | |
|---|---|---|---|
| 4,250,346 A | 2/1981 | Young et al. | |
| 4,339,355 A | 7/1982 | Decker et al. | |
| 5,380,933 A | 1/1995 | Ushikubo et al. | |
| 5,472,925 A * | 12/1995 | Ushikubo et al. | 502/312 |
| 5,750,760 A * | 5/1998 | Ushikubo et al. | 558/319 |
| 5,807,531 A | 9/1998 | Hibst et al. | |
| 5,973,186 A | 10/1999 | Midorikawa et al. | |
| 5,994,580 A | 11/1999 | Takahashi et al. | |
| 6,036,880 A | 3/2000 | Komada et al. | |
| 6,043,185 A | 3/2000 | Cirjak et al. | |
| 6,063,728 A | 5/2000 | Hinago et al. | |
| 6,160,162 A | 12/2000 | Karim et al. | |
| 6,252,122 B1 | 6/2001 | Tenten et al. | |
| 6,383,978 B1 | 5/2002 | Bogan | |
| 6,395,936 B1 | 5/2002 | Arnold et al. | |
| 6,403,525 B1 | 6/2002 | Chaturvedi et al. | |
| 6,407,031 B1 * | 6/2002 | Chaturvedi et al. | 502/311 |
| 6,407,280 B1 | 6/2002 | Chaturvedi et al. | |
| 6,504,053 B1 * | 1/2003 | Chaturvedi et al. | 562/549 |
| 6,620,973 B2 * | 9/2003 | Karim et al. | 568/478 |
| 6,642,174 B2 * | 11/2003 | Gaffney et al. | 502/311 |
| 6,734,136 B2 * | 5/2004 | Chaturvedi et al. | 502/215 |
| 6,825,380 B2 * | 11/2004 | Chaturvedi et al. | 562/542 |
| 6,914,150 B2 * | 7/2005 | Gaffney et al. | 558/319 |
| 6,916,945 B2 * | 7/2005 | Gaffney et al. | 558/320 |
| 6,919,472 B2 * | 7/2005 | Hazin et al. | 558/321 |
| 6,943,135 B2 * | 9/2005 | Gaffney et al. | 502/311 |
| 7,009,075 B2 * | 3/2006 | Hazin | 562/549 |

FOREIGN PATENT DOCUMENTS

| | | |
|---|---|---|
| CN | 1159960 | 9/1997 |
| EP | 0962253 A2 | 12/1999 |
| JP | 6218286 | 8/1994 |
| JP | 10045664 | 2/1998 |
| JP | 10057813 | 3/1998 |
| JP | 10120617 | 5/1998 |
| JP | 10310539 | 11/1998 |
| JP | 11114418 | 4/1999 |
| JP | 2000246108 | 9/2000 |
| WO | WO 01/98246 A1 | 12/2001 |

* cited by examiner

Primary Examiner—Cam N. Nguyen
(74) Attorney, Agent, or Firm—Jim Wheelington

(57) ABSTRACT

A catalyst composition having the formula:

$$Mo_1V_aSb_bNb_cM_dO_x$$

wherein M is gallium, bismuth, silver or gold, a is 0.01 to 1, b is 0.01 to 1, c is 0.01 to 1, d is 0.01 to 1 and x is determined by the valence requirements of the other components. Other metals, such as tantalum, titanium, aluminum, zirconium, chromium, manganese, iron, ruthenium, cobalt, rhodium, nickel, platinum, boron, arsenic, lithium, sodium, potassium, rubidium, calcium, beryllium, magnesium, cerium, strontium, hafnium, phosphorus, europium, gadolinium, dysprosium, holmium, erbium, thulium, terbium, ytterbium, lutetium, lanthanum, scandium, palladium, praseodymium, neodymium, yttrium, thorium, tungsten, cesium, zinc, tin, germanium, silicon, lead, barium or thallium may also be components of the catalyst. This catalyst is prepared by co-precipitation of metal compounds which are calcined to form a mixed metal oxide catalyst that can be used for the selective conversion of an alkane to an unsaturated carboxylic acid in a one-step process.

22 Claims, No Drawings

CATALYST COMPOSITION FOR THE SELECTIVE CONVERSION OF ALKANES TO UNSATURATED CARBOXYLIC ACIDS, METHOD OF MAKING AND METHOD OF USING THEREOF

BACKGROUND OF THE INVENTION

1. Field of the Invention

This invention relates to a process for producing an unsaturated carboxylic acid from an alkane. In particular, this invention relates to a process for producing acrylic acid from propane by a single step vapor phase oxidation reaction.

2. Description of the Prior Art

The production of an unsaturated carboxylic acid, such as acrylic acid or methacrylic acid, is conventionally done by catalytically reacting an olefin, such as propylene or isobutylene, with oxygen to form an alkenylaldehyde, such as acrolein or methacrolein, which is subsequently catalytically reacted with oxygen. Alkanes, such as propane, have advantages of cost and of availability over olefins. Furthermore, a one step process would have advantages over the present commercial process.

There are instances of producing acrylic acid and other unsaturated carboxylic acids from propane and other alkanes in a one step vapor phase catalytic oxidation reaction. U.S. Pat. No. 5,380,933 discloses a method for producing an unsaturated carboxylic acid, such as acrylic acid, with a mixed metal oxide catalyst containing molybdenum, vanadium, tellurium, and at least one of niobium, tantalum, tungsten, titanium, aluminum, zirconium, chromium, manganese, iron, ruthenium, cobalt, rhodium, nickel, palladium, platinum, antimony, bismuth, boron, indium and cerium. Neither gallium, silver nor gold was disclosed as a component of the catalyst. There was no suggestion to select antimony over the other possible components for the catalyst. Tellerium is a necessary component of this prior art catalyst.

Japanese published patent application H10-57813 discloses a metal oxide catalyst of molybdenum, vanadium, tellurium and/or antimony and an element selected from niobium, tantalum, tungsten, titanium, aluminum, zirconium, chromium, manganese, iron, ruthenium, cobalt, rhodium, nickel, palladium, platinum, bismuth, boron, indium, phosphorus, rare earth elements, alkali metals, alkali-earth metals. Neither gallium, silver nor gold was disclosed as a component of the catalyst. There was no suggestion to select bismuth over the other possible components for the catalyst.

Japanese published patent application H10-45664 discloses a catalyst of oxides of molybdenum, vanadium, antimony and an element selected from niobium, tantalum, tungsten, titanium, zirconium, chromium, iron, manganese, ruthenium, cobalt, rhodium, nickel, palladium, platinum, boron, indium, alkali metals, alkaline earth metals, and rare earth elements. Neither gallium, bismuth, silver nor gold was disclosed as a component of the catalyst.

European published patent application 0 962 253 discloses a catalyst having oxides of molybdenum, tungsten, iron, niobium, tantalum, zirconium, ruthenium and mixtures thereof; vanadium, cerium, chromium and mixtures, thereof; tellurium, bismuth, antimony, selenium, and mixtures thereof; and niobium, tantalum, tungsten, titanium, aluminum, zirconium, chromium, manganese, iron, ruthenium, cobalt, rhenium, nickel, palladium, platinum, antimony, bismuth, boron, indium, cerium and mixtures thereof. Neither gallium, silver nor gold was disclosed as a component of the catalyst. There was no suggestion to select antimony or bismuth over the other possible components for the catalyst.

Japanese issued patent no. 10-120,617 discloses a supported catalyst having oxides of molybdenum, vanadium, antimony, one of niobium, tantalum, tin, tungsten, titanium, nickel, iron, chromium or cobalt, and at least one of sodium, potassium, rubidium, cesium, phosphorus and arsenic. Neither gallium, bismuth, silver nor gold was disclosed as a component of the catalyst.

Japanese published patent application H6-218286 disclosed a heteropolyacid catalyst having oxides of phosphorus, molybdenum, vanadium, at least one of arsenic and antimony, and at least one of tin, lead, cerium, cobalt, iron, zirconium, thorium, tungsten, germanium, nickel, rhenium, bismuth, chromium, boron, magnesium, calcium, barium, strontium, selenium, tellurium, silver, aluminum, zinc, copper, titanium, potassium, rubidium, cesium and thallium. Neither gallium, gold nor niobium was disclosed as a component of the catalyst. There was no suggestion to select antimony and silver over the other possible components for the catalyst.

U.S. Pat. Nos. 6,160,162 and 6,114,278 disclose a calcined catalyst having molybdenum, vanadium, gallium, palladium, niobium and at least one of lanthanum, tellurium, germanium, zinc, silicon, indium and tungsten. Neither antimony, bismuth, gold nor silver was disclosed as a component of the catalyst.

U.S. Pat. Nos. 5,994,580 and 6,060,422 discloses a process for producing acrylic acid from propane and oxygen with a mixed metal oxide catalyst containing molybdenum, vanadium, antimony and at least one of niobium, tantalum, tin, tungsten, titanium, nickel, iron, chromium and cobalt. Neither gallium, bismuth, silver nor gold was disclosed as a component of the catalyst.

Japanese patent no. 11114418 discloses a catalyst having oxides of niobium, molybdenum, antimony, at least one of phosphorus, arsenic, boron, silicon and germanium and at least one of potassium, cesium, rubidium, calcium, magnesium, tellurium, chromium, manganese, iron, cobalt, nickel, copper, silver, lead, bismuth, aluminum, gallium, indium, tin, zinc, lanthanum, cerium, yttrium, tungsten, tantalum, ruthenium, rhodium, palladium, platinum, iridium, osmium, rhenium and hafnium. Neither gold nor vanadium was disclosed as a component of the catalyst. There was no suggestion to select gallium, bismuth or silver over the other possible components for the catalyst.

Chinese patent application 1,159,960 discloses bismuth based catalysts with vanadium, niobium, or tantalum and chromium, molybdenum or tungsten, optionally with lithium, sodium, potassium, copper, silver or gold. Neither antimony nor gallium disclosed as a component of the catalyst. There was no suggestion to select gold or silver over the other possible components for the catalyst.

U.S. Pat. No. 4,339,355 discloses a catalyst having molybdenum, vanadium and niobium with chromium, copper, manganese or yttrium. Neither antimony, gallium, gold nor silver was disclosed as a component of the catalyst.

U.S. Pat. No. 6,252,122 discloses a catalyst having molybdenum, bismuth and phosphorus with vanadium, niobium, tantalum, chromium, tungsten, gallium, cerium or lanthanum; lithium, sodium, potassium, rubidium, cesium, copper, silver, gold, palladium or platinum; tin, lead, antimony, bismuth, tellurium, iron, cobalt or nickel; and silicon, aluminum, titanium or zirconium. There was no suggestion to select gallium or gold over the other possible components for the catalyst.

U.S. Pat. No. 5,807,531 discloses a catalyst having molybdenum and vanadium with tungsten, niobium, titanium, zirconium, hafnium, tantalum, chromium, silicon or germanium. Neither antimony, gallium, bismuth, silver nor gold was disclosed as a component of the catalyst.

Japanese patent application no. 246,108 (2000) discloses a catalyst having molybdenum, vanadium and antimony with niobium or tantalum and silver, zinc, tin, lead, arsenic, copper, thallium or selenium. Neither gallium, bismuth nor gold was disclosed as a component of the catalyst. There was no suggestion to select silver over the other possible components for the catalyst.

U.S. Pat. Nos. 6,114,278 and 6,160,162 disclose a catalyst for producing acrylic acid by catalytic vapor phase partial oxidation of propane in one stage. The catalyst contains molybdenum, vanadium, gallium, palladium, niobium and at least one of lanthanum, tellurium, germanium, zinc, silicon, indium or tungsten. There was no disclosure of antimony, bismuth, silver or gold as a component of the catalyst.

PCT/EP01/06821 (WO01/98246) discloses a method of producing acrylic acid with a catalyst containing molybdenum, vanadium and tellurium or antimony and at least one of niobium, tantalum, tungsten, titanium, aluminum, zirconium, chromium, manganese, iron, ruthenium, cobalt, rhodium, nickel, palladium, gallium, platinum, bismuth, boron or cerium. Neither silver nor gold was disclosed as a component of the catalyst of this invention. There was no suggestion to select gallium and antimony over the other possible components. There was no working example of a catalyst containing antimony or gallium.

U.S. Pat. No. 6,383,978 discloses a catalyst for vapor phase oxidation of an alkane to an unsaturated carboxylic acid and for vapor phase ammoxidation of an alkane to an unsaturated nitrile. The catalyst contains molybdenum, vanadium, at least one of tellurium, antimony, tin, germanium or bismuth, at least one of niobium, tantalum, titanium, aluminum, zirconium, chromium, manganese, iron, ruthenium, cobalt, rhodium, nickel, platinum, boron, indium, arsenic, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, lanthanum, scandium, gold, silver, palladium, gallium, praseodymium, rhenium, iridium, neodymium, yttrium, samarium, terbium, tungsten, cerium, copper or zinc, and at least one of selenium or bismuth. There was no suggestion to select gallium, gold, silver and antimony over the other possible components. The catalyst of this invention must contain selenium or bismuth.

U.S. Pat. No. 6,407,280 discloses a catalyst for oxidation of propane or isobutane to acrylic acid or methacrylic acid. The catalyst contains molybdenum or tungsten; vanadium or cerium; tellurium, antimony or selenium; optionally at least one of niobium, tantalum, titanium, aluminum, zirconium, chromium, manganese, iron ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, radium, hafnium, lead, phosphorus, promethium, europium, gadolinium, dysprosium, holmium, erbium, thulium, ytterbium, and lutetium; and at least one of nickel, palladium, copper, silver or gold. Gallium was not disclosed as a component of the catalyst of this invention. There was no suggestion to select antimony over the other possible components. There was no working example of a catalyst containing antimony or gallium.

U.S. Pat. No. 6,403,525 disclosed a catalyst for the oxidation or ammoxidation of alkanes. The catalyst contains molybdenum, vanadium, at least one of tellurium, antimony, tin, germanium or bismuth, at least one of niobium, tantalum, titanium, aluminum, zirconium, chromium, manganese, iron, ruthenium, cobalt, rhodium, nickel, platinum, boron, arsenic, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, lanthanum, scandium, gold, silver, palladium, gallium, praseodymium, rhenium, iridium, neodymium, yttrium, samarium, thorium, tungsten, cerium, copper, or zinc and at least one of indium or rhenium. There was no suggestion to select gallium, bismuth, silver or gold and antimony over the other possible components. The catalyst of this invention must contain indium or rhenium.

Catalyst with similar compositions have been used for processes other than those for producing acrylic acid and other unsaturated carboxylic acids from propane and other alkanes in a one step vapor phase catalytic oxidation reaction.

U.S. Pat. No. 4,250,346 discloses a catalyst for catalytically oxyhydrogenating ethane to ethylene, said catalyst having molybdenum with chromium, manganese, niobium, tantalum, titanium, vanadium or tungsten or bismuth, cerium, cobalt, copper, iron, potassium, magnesium, nickel, phosphorus, lead, antimony, silicon, tin, thallium or uranium. Neither gallium, silver nor gold was disclosed as a component of the catalyst. There was no suggestion to select vanadium, niobium and antimony over the other possible components for the catalyst.

Japanese patent application no. 10-310,539 discloses a catalyst to form propylene from propane, said catalyst having molybdenum, vanadium and niobium. Neither gallium, bismuth, silver nor gold was disclosed as a component of the catalyst.

U.S. Pat. No. 6,043,185 disclosed a catalyst for making acrylonitrile or methacrylonitrile by vapor phase catalyzed reaction of propane or isobutane with oxygen and ammonia. This catalyst contained molybdenum, vanadium, antimony, gallium and at least one of from arsenic, tellurium, selenium, niobium, tantalum, tungsten, titanium, zirconium, chromium, manganese, iron, ruthenium, cobalt, rhodium, nickel, palladium, platinum, boron, indium, cerium, rhenium, iridium, germanium, tin, bismuth, yttrium, praseodymium, an alkali metal and an alkaline earth metal, a is 1; b is 0.0–0.99; c is 0.01–0.9; d is 0.01–0.5; e is 0.0–1.0; and x is determined by the oxidation state of the cations present and the catalyst is preferably free of tellurium (less than 0.01). For a feed of propane, ammonia, oxygen, nitrogen and water, a comparative example without gallium showed selectivities to acrylonitrile of 50.7% and to acrylic acid of 1.5% and examples of the gallium promoted catalyst showed selectivities to acrylonitrile of 45.8–60.3% and to acrylic acid of 0.4 to 3.4%. Neither silver nor gold was disclosed as a component of the catalyst. There was no suggestion to select bismuth over the other possible components for the catalyst.

U.S. Pat. No. 6,036,880 discloses oxidation of propane with a catalyst containing molybdenum, vanadium, niobium and tellurium and/or antimony in which the niobium was dissolved in a particular amount of dicarboxylic acid. Gallium, bismuth, silver and gold were not disclosed as components of the catalyst.

U.S. Pat. Nos. 5,973,186 and 6,080,882 discloses a catalyst for producing an unsaturated nitrile from an alkane by ammoxidation which contains molybdenum, vanadium, niobium, either tellurium or antimony, and, optionally, tantalum, tungsten, titanium, zirconium, hafnium, iron, chromium, manganese, rhenium, ruthenium, cobalt, rhodium, nickel, palladium, osmium, iridium, platinum, copper, silver, zinc, cadmium, boron, aluminum, gallium, indium, thallium, germanium, tin, lead, phosphorus, bismuth, selenium, scandium, yttrium, lanthanum, cerium, praseodymium, neodymium, samarium, gadolinium, alkali metals and alkaline earth metals. There was no suggestion to select gallium, bismuth or silver over the other possible components. Gold was not disclosed as a component of the catalyst.

U.S. Pat. No. 6,063,728 disclosed an ammoxidation catalyst for producing acrylonitrile or methacrylonitrile. The catalyst contains molybdenum, vanadium, niobium and tellurium or antimony and at least one of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals. There was no suggestion to select gallium, silver and antimony over the other possible components. There was no disclosure of gold as a component of the catalyst.

U.S. Pat. No. 6,395,936 disclosed a catalyst of oxides of bismuth, tellurium, antimony, tin and/or copper and molybdenum and/or tungsten and of oxides of an alkali metal, thallium and/or samarium; an alkaline earth metal, nickel, cobalt, copper, manganese, zinc, tin, cadmium, and/or mercury; iron, chromium, cerium and/or vanadium; phosphorus, arsenic, boron and/or antimony; a rare earth metal, titanium, zirconium, niobium, tantalum, rhenium, ruthenium, rhodium, silver, gold, aluminum, gallium, indium, silicon, germanium, lead, thorium and/or uranium and molybdenum and/or tungsten. There was no suggestion to select vanadium, silver, gold, gallium, niobium and antimony over the other possible components.

SUMMARY OF THE INVENTION

This invention is a catalyst for use in a one step process for producing an unsaturated carboxylic acid, such as acrylic acid or methacrylic acid, from an alkane, such as propane or isobutane, a method of making a catalyst and a method of producing an unsaturated carboxylic acid, such as acrylic acid or methacrylic acid, from an alkane, such as propane or isobutane. The catalyst is a composition of the general formula:

$$Mo_1V_aSb_bNb_cM_dO_x$$

wherein M is one or more of gallium, bismuth, silver or gold, a is 0.01 to 1, preferably 0.01 to 0.75, most preferably 0.1 to 0.5; b is 0.01 to 1, preferably 0.01 to 0.5, most preferably 0.1 to 0.5; c is 0.01 to 1, preferably 0.01 to 0.5, most preferably 0.01 to 0.1; d is 0.01 to 1, preferably 0.01 to 0.5, most preferably 0.01 to 0.1, and x is determined by the valence requirements of the other components. The catalyst composition may be represented by the formula:

$$Mo_1V_aSb_bNb_cM_dM'_eO_x$$

wherein M' is one or more elements from tantalum, titanium, aluminum, zirconium, chromium, manganese, iron, ruthenium, cobalt, rhodium, nickel, platinum, boron, arsenic, lithium, sodium, potassium, rubidium, calcium, beryllium, magnesium, cerium, strontium, hafnium, phosphorus, europium, gadolinium, dysprosium, holmium, erbium, thulium, terbium, ytterbium, lutetium, lanthanum, scandium, palladium, praseodymium, neodymium, yttrium, thorium, tungsten, cesium, zinc, tin, germanium, silicon, lead, barium and thallium and e is 0.0 to 1, preferably 0.0 to 0.5, most preferably 0.0 to 0.1.

This catalyst is prepared by co-precipitation of compounds of molybdenum, vanadium, antimony, niobium, and of gallium, bismuth, silver or gold and, optionally, other elements to form a mixed metal oxide catalyst. This catalyst can be used for the selective conversion of an alkane to an unsaturated carboxylic acid in a one-step process.

DESCRIPTION OF EMBODIMENTS OF THE INVENTION

This invention is generally a mixed metal oxide catalyst and, more specifically, a molybdovanadate catalyst. The catalyst of the present invention is a mixture of oxides of molybdenum, vanadium, antimony, niobium and either gallium, bismuth, silver or gold of the general formula:

$$Mo_1V_aSb_bNb_cM_dO_x$$

wherein M is one or more of gallium, bismuth, silver or gold, a is 0.01 to 1, preferably 0.01 to 0.75, most preferably 0.1 to 0.5; b is 0.01 to 1, preferably 0.01 to 0.5, most preferably 0.1 to 0.5; c is 0.01 to 1, preferably 0.01 to 0.5, most preferably 0.01 to 0.1; d is 0.01 to 1, preferably 0.01 to 0.5, most preferably 0.01 to 0.1, and x is determined by the valence requirements of the other components. Preferably, M is gallium.

The catalyst of the present invention may have the composition described in the following formula:

$$Mo_1V_aSb_bNb_cM_dM'_eO_x$$

wherein optional element M' may be one or more selected from tantalum, titanium, aluminum, zirconium, chromium, manganese, iron, ruthenium, cobalt, rhodium, nickel, platinum, boron, arsenic, lithium, sodium, potassium, rubidium, calcium, beryllium, magnesium, cerium, strontium, hafnium, phosphorus, europium, gadolinium, dysprosium, holmium, erbium, thulium, terbium, ytterbium, lutetium, lanthanum, scandium, palladium, praseodymium, neodymium, yttrium, thorium, tungsten, cesium, zinc, tin, germanium, silicon, lead, barium and thallium and e is 0.0 to 1, preferably 0.0 to 0.5, most preferably 0.0 to 0.1.

Specific examples of the catalyst of the present invention are $Mo_1V_{0.3}Sb_{0.15}Nb_{0.05}Ga_{0.03}O_x$, $Mo_1V_{0.3}Sb_{0.08}Nb_{0.05}Ga_{0.03}O_x$, $Mo_1V_{0.3}Nb_{0.05}Sb_{0.15}Bi_{0.03}O_x$, $Mo_1V_{0.03}Sb_{0.15}Nb_{0.05}Ag_{0.06}O_x$, $Mo_1V_{0.03}Sb_{0.15}Nb_{0.05}Au_{0.015}O_x$ and $Mo_1V_{0.3}Nb_{0.05}Sb_{0.15}Ga_{0.03}W_{0.012}O_x$.

This catalyst may be used in a one-step process for producing an unsaturated carboxylic acid, such as acrylic acid or methacrylic acid, from an alkane, such as propane or isobutane. The alkane is preferably one having three to eight carbon atoms and is most preferable propane or isobutane. The process is preferably a vapor phase reaction in which the catalyst in brought into contact with an alkane and oxygen. The molar ratio of alkane:oxygen is preferably in the range of from 0.01:1 to 10:1. The contact time for the reactants preferably is in the range of from 0.1 to 10 seconds, preferably 0.1 to 5 seconds. Steam may be added to the reaction gases. If steam is used, the molar ratio of alkane: steam is in the range from 0.05:1 to 10:1. In addition, an inert gas such as nitrogen, argon or helium may be used a carrier medium. If a carrier medium is used, the molar ratio of alkane:carrier preferably is in the range from 0.01:1 to 10:1.

The reaction temperature for the method of using the present invention is 320–450° C., preferably 350–400° C. The reaction pressure is 0 to 100 psig, preferably 5 to 50 psig.

The method of using the present invention will, in addition to the unsaturated carboxylic acid, produce byproducts, including an olefin. For example, when the alkane is propane, byproducts of carbon monoxide, carbon dioxide, acetic acid and propylene will be formed. The olefin, such as propylene, may be separated from the other byproducts and recycled into the feed stream. The catalyst and process of the present invention can convert an olefin into an unsaturated carboxylic acid, e.g., propylene into acrylic acid.

In the alternative, the olefin may be separated from the other byproducts and converted to an unsaturated carboxylic acid in a separate process using known catalysts for converting an olefin into an unsaturated carboxylic acid or used in other processes to produce other products.

The catalyst of the present invention may be used as an unsupported catalyst or a supported catalyst. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

Preferably, the catalyst is prepared from a solution of water-soluble compounds of each of the component metals. If the compounds are insoluble in water, a slurry or suspension may be formed and thoroughly dispersed or mixed. In the alternative, a solvent other than water, such as an acid or an alkali, may be used. Heat may be applied to facilitate dissolution in the solvent. Generally, a mixture of compounds of the elements, such as salts of other complexes, in the approximate desired gram-atom ratio is dissolved to form a solution. The solution can be heated to help react the compounds and to form desired phases. Hydrothermal techniques known in the art can be applied to use elevated temperatures and pressures in solution. The liquid solvent is removed and the resulting catalyst composition is dried and then calcined.

Suitable precursor molybdenum compounds are molybdenum salts, such as ammonium paramolybdate, molybdenum oxides, molybdic acids or molybdenum chlorides. Suitable precursor vanadium compounds are vanadium salts, such as ammonium metavanadate, vanadium oxides, vanadium oxalates or vanadium sulfates.

Suitable precursor antimony compounds are antimony oxides, antimony chlorides, antimony sulfate, antimony tartrate and antimony acetate.

Suitable precursor niobium compounds are niobium oxalate, ammonium niobium oxalate, niobium oxide, hydrous niobium oxide or niobic acid. Oxalic acid and niobic acid may be dissolved in water to obtain a solution. With respect to the obtained solution, it is preferred that the molar ratio of oxalic acid to niobium is in the range of from 1:1 to 12:1, preferably from 3:1 to 6:1. A dicarboxylic acid other than oxalic acid, such as malonic acid, succinic acid, glutaric acid and adipic acid, or a tricarboxylic acid, such as citric acid, may be used with or without niobic acid to form a solution.

Suitable precursor gallium compounds are gallium oxide, gallium nitrate, gallium chloride, gallium acetylacetonate and gallium sulfate.

Suitable precursor silver compounds are silver oxide, silver acetate, silver carbonate, silver nitrate or silver halides, such as silver chloride.

Suitable precursor bismuth compounds are bismuth acetate, bismuth hydroxide, bismuth nitrate, bismuth nitrate hydrates, bismuth(III) nitrate oxide, bismuth(III) oxide, bismuth citrate, bismuth fluoride, bismuth chloride, bismuth bromide, bismuth iodide, bismuth(III) oxychloride, bismuth (III) oxynitrate, bismuth(III) phosphate, bismuth subcarbonate, bismuth subnitrate, bismuth subnitrate monohydrate, bismuth subsalicylate and bismuth(III) sulfide.

Suitable precursor gold compounds are gold bromide, gold chloride, gold hydroxide, gold iodide or hydrogen tetrachloroaurate.

Suitable precursor compounds of other metals, such as tantalum, titanium, aluminum, zirconium, chromium, manganese, iron, ruthenium, cobalt, rhodium, nickel, platinum, boron, arsenic, lithium, sodium, potassium, rubidium, calcium, beryllium, magnesium, cerium, strontium, hafnium, phosphorus, europium, gadolinium, dysprosium, holmium, erbium, thulium, terbium, ytterbium, lutetium, lanthanum, scandium, palladium, praseodymium, neodymium, yttrium, thorium, tungsten, cesium, zinc, tin, germanium, silicon, lead, barium and thallium, are salts such as oxalates, tartrates, citrates, nitrates, halides, carbonates, bicarbonates, hydroxides, oxides and the like with nitrate and oxalate salts being preferred when appropriate and available. For phosphorus and arsenic, appropriate precursor compounds would include ammonium hydrogen phosphate, ammonium phosphate, phosphorus pentoxide, phosphoric acid, phosphorous acid, arsenic acid and arsenic oxide The liquid solvent may be removed by filtration, evaporation or centrifuge. If heat is used during removal of the liquid, preferably the temperature will be in the range from 40 to 100° C. Drying the catalyst composition is by methods known in the art. Spray drying may be used as a means to remove the liquid solvent and dry the catalyst in a single operation. Typical outlet temperature for spray drying the catalyst of this invention is 90–105° C. After the catalyst composition is dried, preferably it is heat treated in air at a temperature in the range of 250–350° C. for 1 to 10 hours. Calcination of the catalyst composition preferably occurs in an inert gas, such as argon or nitrogen, at a temperature in the range of 550–650° C. for 1 to 10 hours. The solid catalyst may be further prepared by high-energy ballmilling with a planetary ballmill or lower energy grinding or crushing means to obtain desired crystallite size, particle size, particle shape and/or particle size distribution.

There are two factors which contribute to a catalyst being useful for oxidation of an alkane to an unsaturated carboxylic acid. The first factor is the degree to which the alkane is converted (% conversion). The second is the extent to which the desired product is obtained (% selectivity). The product of these two factors in turn determine the overall yield of the catalyst in the oxidation of an alkane to an unsaturated carboxylic acid. The catalyst of the catalyst of the present invention can attain a conversion of propane of 50% and a selectivity to acrylic acid of 56.2% for an overall yield of 28.2%.

The invention having been generally described, the following examples are given as particular embodiments of the invention and to demonstrate the practice and advantages thereof. It is understood that the examples are given by way of illustration and are not intended to limit the specification or the claims to follow in any manner.

COMPARATIVE EXAMPLE 1

A mixed metal oxide with a nominal composition of $Mo_1V_{0.3}Nb_{0.05}Sb_{0.15}O_x$ was prepared as follows:

Solution A: Ammonium vanadate (7.95 g) was dissolved in 165 mL water at 90° C. Antimony(III) oxide (4.92 g) was added and the mixture was purged with nitrogen and heated at 92° C. for about 4.5 hrs. Heating was discontinued and the mixture was cooled overnight under nitrogen. Water (105 mL) was removed by rotary evaporation. Ammonium paramolybdate (40.0 g) was added and the mixture was stirred under nitrogen for 4.5 hrs. Solution B: Niobium oxalate monooxalate (7.12 g) was stirred in 40 mL water for 5 hrs. Solution B was added to solution A and the resulting mixture was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 1 g of this catalyst was tested for propane oxidation with a feed having a propane/O2/N2/water ratio of 1/1.6/14.4/15. The results are shown in table 1.

COMPARATIVE EXAMPLE 2

1 g of the mixed metal oxide prepared in comparative example 1 was tested for propane oxidation with a feed having a propane/O2/N2/water ratio of 1/1.6/14.4/15. The results are shown in table 1.

COMPARATIVE EXAMPLE 3

1 g of the mixed metal oxide prepared in comparative example 1 was tested for propane oxidation with a feed having a propane/O2/N2/water ratio of 1/1.6/14.4/15. The results are shown in table 1.

EXAMPLE 1

A mixed metal oxide with a nominal composition of $Mo_1V_{0.3}Nb_{0.05}Sb_{0.15}Ga_{0.03}Ox$ was prepared as follows:

Solution A: Ammonium vanadate (7.95 g) was dissolved in 165 mL water at 90° C. Antimony(III) oxide (4.92 g) was added and the mixture was heated at 98° C. for about 5 hrs. Heating was discontinued and the mixture was cooled. Some of the water was removed by rotary evaporation. Ammonium paramolybdate (40.0 g) was added and the mixture was stirred overnight. Solution B: Niobium oxalate monooxalate (7.12 g) was stirred in 40 mL water overnight. Solution C: Gallium oxide (0.645 g) was stirred in 20 mL water overnight. Solution B was added to solution A followed by solution C, and the resulting mixture was spray dried after 20 minutes to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 1 g of this catalyst was tested for propane oxidation with a feed having a propane/O2/N2/water ratio of 1/1.6/14.4/15. The results are shown in table 1.

EXAMPLE 2

1 g of the mixed metal oxide prepared in example 1 was tested for propane oxidation with a feed having a propane/O2/N2/water ratio of 1/1.6/14.4/15. The results are shown in table 1.

EXAMPLE 3

A mixed metal oxide with a nominal composition of $Mo_1V_{0.3}Nb_{0.05}Sb_{0.08}Ga_{0.03}Ox$ was prepared as follows Solution A: Ammonium vanadate (7.95 g) was dissolved in 165 mL heating. Antimony(III) oxide (2.64 g) was added and the mixture was heated at 92° C. for about 7 hrs. Heating was discontinued, N2 purge was added and the mixture was cooled overnight. Some of the water (153g) was removed by rotary evaporation. Water (20 mL) was added. Ammonium paramolybdate (40.0 g) was added and the mixture was stirred for 3.5 hrs. Solution B: Niobium oxalate monooxalate (7.12 g) was stirred in 40 mL water overnight. Solution C: Gallium oxide (0.645 g) was stirred in 20 mL water overnight. Solution B was added to solution A followed by solution C, and the resulting mixture was spray dried after 5 minutes to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 1 g of this catalyst was tested for propane oxidation with a feed having a propane/O2/N2/water ratio of 1/1.6/14.4/15. The results are shown in table 1.

EXAMPLE 4

A mixed metal oxide with a nominal composition of $Mo_1V_{0.3}Nb_{0.05}Sb_{0.15}Ga_{0.03}W_{0.012}O_x$ was prepared as follows:

Solution A: Ammonium vanadate (7.95 g) was dissolved in 170 mL with heating. Antimony(III) oxide (4.92 g) was added and the mixture was heated at 96–100° C. for about 4 hrs under nitrogen flow. Heating was discontinued, and the mixture was cooled overnight under nitrogen. Ammonium paramolybdate (40.0 g) was added. Some of the water (100 g) was removed by rotary evaporation. The mixture was stirred for a total of 1.5 hrs. Solution B: Niobium oxalate monooxalate (7.12 g) was stirred in 40 mL water overnight. Solution C: Gallium oxide (0.654 g) was stirred in 20 mL water overnight. Solution B was added to solution A followed by solution C, and the resulting mixture was spray dried after 20 minutes to give a solid catalyst precursor. The catalyst precursor was heated in air at 120° C. for 1 hr, then decomposed at 300° C. for 5 hrs. 9.23 g of this decomposed mixture was impregnated with 0.156 g of ammonium tungstate in 5 mL water. The solid was dried at 50° C. then at 300° C. for 30 minutes before it was calcined in argon at 600° C. for 2 hrs. The resulting powder was ground pressed and sieved to 18/35 mesh. 1 g of this catalyst was tested for propane oxidation with a feed having a propane/O2/N2/water ratio of 1/1.6/14.4/15. The results are shown in table 1.

EXAMPLE 5

1 g of the mixed metal oxide prepared in example 4 was tested for propane oxidation with a feed having a propane/O2/N2/water ratio of 1/3.0/27/14. The results are shown in table 1.

EXAMPLE 6

A mixed metal oxide with a nominal composition of $Mo_{V0.3}Nb_{0.05}Sb_{0.15}Ag_{0.06}Ox$ was prepared as follows:

Solution A: Ammonium vanadate (7.95 g) was dissolved in 165 mL water with heating. Antimony(III) oxide (4.92 g) was added and the mixture was purged with nitrogen and heated at 95° C. for about 5 hrs. Heating was discontinued and the mixture was cooled overnight under nitrogen. Some of the water (130 mL) was removed by rotary evaporation. Ammonium paramolybdate (40.0 g) was added and the mixture was stirred for 4 hrs under nitrogen. Solution B: Niobium oxalate monooxalate (7.12 g) was stirred in 40 mL water overnight. Solution C: silver nitrate (2.31 g) was dissolved in 20 mL water. Solution B was added to solution A followed by solution C, and the resulting mixture kept under nitrogen for 20 minutes until it was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 2.6 g of this catalyst was tested for propane oxidation with a feed having a propane/O2/N2/water ratio of 1/1.6/14.4/15. The results are shown in table 1.

EXAMPLE 7

1.8 g of the mixed metal oxide prepared in example 6 was tested for propane oxidation with a feed having a propane/O2/N2/water ratio of 1/0.5/4.5/1.3. The results are shown in table 1.

EXAMPLE 8

A mixed metal oxide with a nominal composition of $Mo_1V_{0.03}Nb_{0.05}Sb_{0.15}Au_{0.015}Ox$ was prepared as follows:

Solution A: Ammonium vanadate (7.95 g) was dissolved in 165 mL water with heating. Antimony(III) oxide (4.92 g) was added and the mixture heated at 94° C. for about 4.5 hrs. Heating was discontinued and the mixture was cooled overnight. Some of the water (105 mL) was removed by rotary evaporation. Ammonium paramolybdate (40.0 g) was added and the mixture was stirred for 2.5 hrs under nitrogen. Solution B: Niobium oxalate monooxalate (7.12 g) was stirred in 40 mL water overnight. Solution C: Gold hydroxide (0.843 g) was suspended in 60 mL water. Solution B was added to solution A followed by solution C, and the resulting mixture was stirred for 15 minutes until it was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 2.7 g of this catalyst was tested for propane oxidation with a feed having a propane/O2/N2/water ratio of 1/1.6/14.4/15. The results are shown in table 1.

EXAMPLE 9

2.7 g of the mixed metal oxide prepared in example 8 was tested for propane oxidation with a feed having a propane/O2/N2/water ratio of 1/3.0/27/14. The results are shown in table 1.

EXAMPLE 10

2.7 g of the mixed metal oxide prepared in example 8 was tested for propane oxidation with a feed having a propane/O2/N2/water ratio of 1/1.6/14.4/15. The results are shown in table 1.

EXAMPLE 11

A mixed metal oxide with a nominal composition of $Mo_1V_{0.3}Nb_{0.05}Sb_{0.15}Bi_{0.03}O_x$ was prepared as follows Solution A: Ammonium vanadate (7.95 g) was dissolved in 165 mL water with heating. Antimony(III) oxide (4.92 g) was added and the mixture was heated at 95° C. for 4 hrs. Heating was discontinued and the mixture was cooled under nitrogen atmosphere overnight. Water (109 g) was removed by rotary evaporation. Ammonium paramolybdate solid (40.0 g) was added and the mixture was stirred for 4 hrs. Solution B: Niobium oxalate mono oxalate (7.12 g) was stirred in 40 mL water for 4 hrs. Solution C: Bismuth nitrate pentahydrate (3.298 g) was suspended in 60 mL water for 4 hrs. Solution B was added to solution A followed by solution C, and the resulting mixture was spray dried after 5 minutes to give a solid catalyst precursor. The catalyst precursor was heated in air at 120° C. for 1 hr, then decomposed at 300° C. for 5 hrs, then calcined in argon at 600° C. for 2 hrs. The resulting powder was ground pressed and sieved to 18/35 mesh. 2.65 g of this catalyst was tested for propane oxidation with a feed having a propane/O2/N2/water ratio of 1/3.0/27/14. The results are shown in table 1.

EXAMPLE 12

1 g of the mixed metal oxide prepared in example Bi1 was tested for propane oxidation with a feed having a propane/O2/N2/water ratio of 1/3.0/27/14. The results are shown in table 1.

For each of the catalysts from the Examples above, the stated weight of catalyst was mixed with a sufficient amount of quartz chips to make a catalyst bed of 5.0 cc in a downflow packed bed reactor. The reactor was heated to a temperature as specified in each example. A mixture of propane, oxygen, nitrogen and steam was supplied to the reactor at a percent by volume and a rate as specified in Table 1. The reaction continued at the pressure specified in Table 1 for at least three hours. The % conversion, the % selectivity to acrylic acid and the productivity (kgAA/m$^3$cat·hr–kilogram of acrylic acid per cubic meter of catalyst per hour) were calculated and are reported in Table 1.

TABLE 1

| Examples | Catalyst Bed TEMP (° C.) | RX Inlet Pressure Psig | Reactant's Residence Time (sec) | GHSV L gas/L cat-hr. | Wt % Propane Conversion | AA Selectivity | AA YIELD | Kg AA/M3Cat-hr |
|---|---|---|---|---|---|---|---|---|
| Comp. Ex. 1 | 400 | 20 | 0.36 | 9703 | 40 | 40.0 | 16.2 | 169.7 |
| Comp. Ex. 2 | 400 | 20 | 0.22 | 15363 | 30 | 45.7 | 13.8 | 216.6 |

TABLE 1-continued

| Examples | Catalyst Bed TEMP (°C.) | RX Inlet Pressure Psig | Reactant's Residence Time (sec) | GHSV L gas/L cat-hr. | Wt % Propane Conversion | AA Selectivity | AA YIELD | Kg AA/M3Cat-hr |
|---|---|---|---|---|---|---|---|---|
| Comp. Ex. 3 | 400 | 20 | 0.27 | 12785 | 33 | 41.4 | 13.8 | 190.4 |
| Ex. 1 | 400 | 32 | 0.27 | 16934 | 47 | 53.3 | 25.3 | 435.3 |
| Ex. 2 | 400 | 20 | 0.31 | 11068 | 51 | 48.8 | 25.0 | 281.5 |
| Ex. 3 | 400 | 20 | 0.30 | 11666 | 37 | 39.1 | 14.4 | 177.0 |
| Ex. 4 | 400 | 32 | 0.33 | 14141 | 31 | 39.5 | 12.3 | 180 |
| Ex. 5 | 380 | 32 | 0.71 | 6760 | 45 | 29.9 | 13.6 | 67 |
| Ex. 6 | 400 | 32 | 1.19 | 3911 | 50 | 56.2 | 28.2 | 118 |
| Ex. 7 | 360 | 20 | 0.44 | 8266 | 13 | 57.1 | 7.6 | 280 |
| Ex. 8 | 400 | 10 | 0.53 | 4614 | 32 | 40.7 | 13.2 | 59.8 |
| Ex. 9 | 400 | 32 | 1.04 | 4457 | 58 | 39.2 | 22.6 | 74.1 |
| Ex. 10 | 400 | 32 | 1.01 | 4602 | 48 | 39.5 | 19.0 | 86.0 |
| Ex. 11 | 380 | 20 | 0.81 | 4372 | 56 | 44.5 | 25.1 | 85.0 |

The Examples above demonstrate the effectiveness of a mixed metal oxide molybdovanadate catalyst containing antimony, niobium and one of gallium, silver or gold in the conversion of an alkane to an unsaturated carboxylic acid in a one-step process. Furthermore, there are benefits in using such a catalyst which contains gallium as shown by the data above in improved propane conversion, acrylic acid selectivity, acrylic acid yield and acrylic acid productivity. With adjusted process conditions, there are benefits in using such a catalyst which contains silver or gold or gallium and tungsten.

Obviously, numerous modifications and variations of the present invention are possible in light of the above teachings. It is therefore to be understood that within the scope of the appended claims, the invention may be practiced otherwise than as specifically described herein.

The catalyst and process of the present invention are applicable to different reaction systems, such as fixed bed, moving bed and fluidized bed reactors. The catalyst particle size and process conditions can be altered for the desired reaction system.

The catalyst of the present invention should be applicable to different processes, such as ammoxidation of alkanes and olefins, e.g., producing acrylonitrile from propane, oxygen and ammonia or producing methacrylonitrile from isobutane, oxygen and ammonia.

What is claimed is:

1. A mixed metal oxide catalyst composition for production of an unsaturated carboxylic acid from an alkane comprising a compound having the formula:

$Mo_1V_aSb_bNb_cGa_dO_x$ wherein Mo is molybdenum, V is vanadium, Sb is antimony, Nb is niobium, Ga is gallium, a is from 0.01 to 1, b is 0.01 to 1, c is 0.01 to 1, d is 0.01 to 1, and x is determined by the valence requirements of the other elements present.

2. The catalyst composition of claim 1 wherein the formula is:

$Mo_1V_aSb_bNb_cGa_dM'_eO_x$ wherein M' is tantalum, titanium, aluminum, zirconium, chromium, manganese, iron, ruthenium, cobalt, rhodium, nickel, platinum, boron, arsenic, lithium, sodium, potassium, rubidium, calcium, beryllium, magnesium, cerium, strontium, hafnium, phosphorus, europium, gadolinium, dysprosium, holmium, erbium, thulium, terbium, ytterbium, lutetium, lanthanum, scandium, palladium, praseodymium, neodymium, yttrium, thorium, tungsten, cesium, zinc, tin, germanium, silicon, lead, barium and thallium and e is 0.0 to 1.

3. The catalyst composition of claim 2 wherein the formula is:

$Mo_1V_aSb_bNb_cGa_dM_{d'}M''_eO_x$ wherein M is bismuth, silver or gold and d' is 0.01 to 1.

4. The catalyst composition of claim 2 wherein M' is tungsten.

5. The catalyst composition of claim 2 wherein e is 0.0 to 0.5.

6. The catalyst composition of claim 5 wherein e is 0.0 to 0.01.

7. The catalyst composition of claim 1 wherein a is 0.01 to 0.75.

8. The catalyst composition of claim 7 wherein a is 0.1 to 0.5.

9. The catalyst composition of claim 6 wherein a is 0.3.

10. The catalyst composition of claim 1 wherein b is 0.01 to 0.5.

11. The catalyst composition of claim 10 wherein b is 0.1 to 0.5.

12. The catalyst composition of claim 11 wherein b is 0.15.

13. The catalyst composition of claim 1 wherein c is 0.01 to 0.5.

14. The catalyst composition of claim 13 wherein c is 0.1 to 0.5.

15. The catalyst composition of claim 14 wherein c is 0.05.

16. The catalyst composition of claim 1 wherein d is 0.01 to 0.5.

17. The catalyst composition of claim 16 wherein d is 0.1 to 0.1.

18. The catalyst composition of claim 17 wherein d is 0.03 to 0.06.

19. The catalyst composition of claim 1 selected from the group consisting of $Mo_1V_{0.3}Sb_{0.15}Nb_{0.05}Ga_{0.03}O_x$, $Mo_1V_{0.3}Sb_{0.08}Nb_{0.05}Ga_{0.03}O_x$, and $Mo_1V_{0.3}Nb_{0.05}Sb_{0.15}Ga_{0.03}W_{0.012}O_x$.

20. The catalyst composition of claim 1 wherein the catalyst composition is supported on an inert support.

21. The catalyst composition of claim 20 wherein the inert support is silica, alumina, niobia, titania, zirconia and mixtures thereof.

22. The catalyst composition of claim 1 wherein the catalyst composition in the form of powder, granules, spheres, cylinders or saddles.

* * * * *

UNITED STATES PATENT AND TRADEMARK OFFICE
CERTIFICATE OF CORRECTION

| | |
|---|---|
| PATENT NO. | : 7,229,946 B2 |
| APPLICATION NO. | : 10/806862 |
| DATED | : June 12, 2007 |
| INVENTOR(S) | : Paulette N. Hazin and Paul E. Ellis, Jr. |

It is certified that error appears in the above-identified patent and that said Letters Patent is hereby corrected as shown below:

On The Title Page, Insert Item
--(60) Related U.S. Application Data
This patent claims the benefit of Provisional Application No. 60/457,117, filed Mar. 24, 2003.--

Signed and Sealed this

Seventeenth Day of March, 2009

JOHN DOLL
*Acting Director of the United States Patent and Trademark Office*